United States Patent
Hong et al.

(10) Patent No.: US 9,926,395 B2
(45) Date of Patent: *Mar. 27, 2018

(54) HYBRID SUPPORTED METALLOCENE CATALYST

(71) Applicant: LG CHEM, LTD., Seoul (KR)

(72) Inventors: Dae Sik Hong, Daejeon (KR); Heon Yong Kwon, Daejeon (KR); Eun Kyoung Song, Daejeon (KR); Yong Ho Lee, Daejeon (KR); Kyung Jin Cho, Daejeon (KR); Ki Soo Lee, Daejeon (KR); Yi Young Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/026,544

(22) PCT Filed: Oct. 15, 2014

(86) PCT No.: PCT/KR2014/009681
§ 371 (c)(1),
(2) Date: Mar. 31, 2016

(87) PCT Pub. No.: WO2015/056975
PCT Pub. Date: Apr. 23, 2015

(65) Prior Publication Data
US 2016/0237187 A1    Aug. 18, 2016

(30) Foreign Application Priority Data

Oct. 18, 2013   (KR) .................. 10-2013-0124518
Oct. 14, 2014   (KR) .................. 10-2014-0138348

(51) Int. Cl.
| | | |
|---|---|---|
| C08F 210/16 | (2006.01) | |
| C08F 4/6592 | (2006.01) | |
| B01J 31/12 | (2006.01) | |
| C07F 17/00 | (2006.01) | |
| C08F 4/64 | (2006.01) | |
| C07F 7/08 | (2006.01) | |
| B01J 31/22 | (2006.01) | |

(52) U.S. Cl.
CPC ............ *C08F 210/16* (2013.01); *B01J 31/12* (2013.01); *C07F 7/0814* (2013.01); *C07F 17/00* (2013.01); *C08F 4/64* (2013.01); *C08F 4/6592* (2013.01); *C08F 4/65927* (2013.01); *B01J 31/2295* (2013.01)

(58) Field of Classification Search
None
See application file for complete search history.

(56) References Cited

U.S. PATENT DOCUMENTS

| 5,032,562 A | 7/1991 | Lo et al. |
|---|---|---|
| 5,525,678 A | 6/1996 | Mink et al. |
| 5,914,289 A | 6/1999 | Razavi |
| 2003/0195306 A1* | 10/2003 | Tsuie ............... C08F 210/02 526/127 |
| 2003/0229188 A1 | 12/2003 | Nagy et al. |
| 2006/0183631 A1 | 8/2006 | Lee et al. |
| 2012/0059135 A1 | 3/2012 | Michiue et al. |
| 2012/0123078 A1 | 5/2012 | Lee et al. |
| 2012/0329966 A1* | 12/2012 | Kwon ............... C08F 10/00 526/131 |
| 2013/0046068 A1 | 2/2013 | Kwon et al. |
| 2014/0206828 A1 | 7/2014 | Kwon et al. |

FOREIGN PATENT DOCUMENTS

| EP | 2374822 A2 | 10/2011 | |
|---|---|---|---|
| EP | 2484443 A2 | 8/2012 | |
| EP | 2837640 A1 | 2/2015 | |
| EP | 3012262 A1 | 4/2016 | |
| JP | 2008-530298 A | 8/2008 | |
| JP | 2013-521398 A | 6/2013 | |
| KR | 1020000069979 A | 11/2000 | |
| KR | 1020040076965 A | 9/2004 | |
| KR | 100521458 B1 | 10/2005 | |
| KR | 1020100028317 A | 3/2010 | |
| KR | 1020100067627 A | 6/2010 | |
| KR | 1020110013286 A | 2/2011 | |
| KR | 1020110035968 A | 4/2011 | |
| KR | 101154508 B1 | 6/2012 | |
| KR | 1020120076156 A | 7/2012 | |
| KR | 1020120087706 A | 8/2012 | |
| WO | 2004-076502 A1 | 9/2004 | |
| WO | 2011-111979 A2 | 9/2011 | |
| WO | WO 2012102572 * | 6/2012 | ............ C08F 299/00 |
| WO | 2013133595 A1 | 9/2013 | |

OTHER PUBLICATIONS

Alexakis, et al., "Mild Protection and Deprotection of Alcohols as Ter-Butyl Ethers in the field of Pheromone Sysnthesis," Tetrahedron Letters, vol. 29, No. 24, pp. 2951-2954 (1988).

\* cited by examiner

*Primary Examiner* — Yun Qian
(74) *Attorney, Agent, or Firm* — Dentons US LLP

(57) ABSTRACT

The present invention relates to a hybrid supported metallocene catalyst. More specifically, the present invention relates to a hybrid supported metallocene catalyst using two or more different types or more of metallocene compounds, among which one type of the metallocene compounds shows a high polymerization activity even when it is supported, and thus the catalyst has an excellent activity and can be utilized in the polymerization of olefinic polymers having ultra-high molecular weight. Based on the hybrid supported metallocene catalyst of the present invention, an olefinic polymer having high molecular weight and the desired physical property can be prepared.

3 Claims, No Drawings

HYBRID SUPPORTED METALLOCENE CATALYST

BACKGROUND OF THE INVENTION (a) Field of the Invention

The present invention relates to a hybrid supported metallocene catalyst. More specifically, the present invention relates to a hybrid supported metallocene catalyst that can be used in the preparation of an olefinic polymer.

CROSS-REFERENCE TO RELATED APPLICATION(S)

This application is a National Stage Application of International Application No. PCT/KR2014/009681, filed Oct. 15, 2014, and claims the benefit of Korean Patent Application No. 10-2014-0138348, filed Oct. 14, 2014, and Korean Patent Application No. 10-2013-0124518, filed Oct. 18, 2013, the contents of which are incorporated herein by reference in their entirety for all purposes as if fully set forth below.

(b) Description of the Related Art

Olefin polymerization catalyst systems can be classified into Ziegler-Natta and metallocene catalyst systems, and these two highly active catalyst systems have been developed in compliance with their characteristics. Ziegler-Natta catalyst has been widely applied to existing commercial processes since it was developed in the 1950's. However, since the Ziegler-Natta catalyst is a multi-active site catalyst in which a plurality of active sites are mixed, it has a feature that molecular weight distribution of polymers is broad. Also, since compositional distribution of comonomers is not uniform, there is a problem that it has a limitation to secure the desired physical properties.

Meanwhile, the metallocence catalyst includes a main catalyst whose main component is a transition metal compound, and an organometallic compound cocatalyst whose main component is aluminium. Such a catalyst is a single-site catalyst which is a homogeneous complex catalyst, and offers a polymer having a narrow molecular weight distribution and an uniform composition distribution of comonomers, depending on the single site characteristics. The stereoregularity, copolymerizing properties, molecular weight, crystallinity and the like of the resulting polymer can be controlled by changing the ligand structure of the catalyst and the polymerization condition.

U.S. Pat. No. 5,032,562 describes a method for preparing a polymerization catalyst by supporting two different transition metal catalysts on one supported catalyst. This patent relates to a method for preparing a bimodal distribution polymer by supporting a Ti-based Ziegler-Natta catalyst which produces a high molecular weight polymer and a Zr-based metallocene catalyst which produces a low molecular weight polymer on one support, and has disadvantages in that the supporting procedure is complicated and the morphology of polymers is deteriorated due to a cocatalyst.

U.S. Pat. No. 5,525,678 discloses a process for using a catalyst system for olefin polymerization in which a metallocene compound and a non-metallocene compound can be simultaneously supported on a support to simultaneously polymerize a high molecular weight polymer and a low molecular weight polymer. However, this patent has disadvantages in that the metallocene compound and the non-metallocene compound must be each separately supported and the support must be pre-treated with various compounds for the supporting reaction.

U.S. Pat. No. 5,914,289 discloses a method of controlling the molecular weight and the molecular weight distribution of polymers using metallocene catalysts which are respectively supported on supports. However, a large amount of solvent and a long period of time are required to prepare the supported catalysts, and the process of supporting metallocene catalysts on the respective supports is troublesome.

Korean Patent Application No. 2003-12308 discloses a method of controlling the molecular weight distribution of polymers by polymerizing while changing a combination of catalysts in a reactor by supporting a bi-nuclear metallocene catalyst and a mononuclear metallocene catalyst on a support with an activating agent. However, this method has a limitation to simultaneously secure the properties of the respective catalysts. In addition, there is a disadvantage that a metallocene catalyst portion is departed from the completed supported catalyst to cause fouling in the reactor.

Therefore, in order to solve the above-mentioned disadvantages, there is a need to develop a method for preparing olefinic polymers with the desired physical properties by easily preparing a supported hybrid metallocene catalyst having an excellent activity.

SUMMARY OF THE INVENTION

Technical Problem

In order to solve the above-mentioned problems of the prior arts, an object of the present invention is to provide a hybrid supported metallocene catalyst capable of preparing an olefinic polymer having excellent activity as well as high molecular weight and desired physical properties.

Technical Solution

In order to achieve the above object, the present invention provides a hybrid supported metallocene catalyst which comprises one or more first metallocene compounds represented by the following Chemical Formula 1, one or more second metallocene compounds selected among the compounds represented by the following Chemical Formula 3 to Chemical Formula 5, a cocatalyst compound and a support.

[Chemical Formula 1]

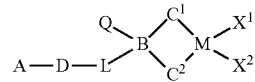

[Chemical Formula 3]

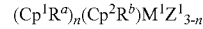

[Chemical Formula 4]

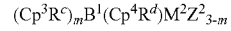

[Chemical Formula 5]

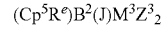

Chemical Formulae 1, 3, 4 and 5 will be described in detail below.

The hybrid supported metallocene catalyst according to the present invention includes two or more different types of metallocene compounds. In particular, since one type of the metallocene compound uses a ligand compound forming a structure in which an indenoindole derivative and/or a fluorene derivative are crosslinked via a bridge, this exhibits a high polymerization activity even when it is supported, and thus it can be utilized in the polymerization of olefinic polymers having ultra-high molecular weight and excellent activity.

DETAILED DESCRIPTION OF THE EMBODIMENTS

Hereinafter, the hybrid supported metallocene catalyst according to specific embodiments of the present invention will be described in detail.

The hybrid supported metallocene catalyst according to the present invention comprises one or more first metallocene compounds represented by the following Chemical Formula 1, one or more second metallocene compounds selected among the compounds represented by the following Chemical Formula 3 to Chemical Formula 5, a cocatalyst compound and a support.

[Chemical Formula 1]

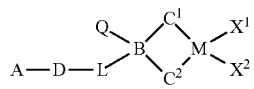

in Chemical Formula 1,

A is hydrogen, halogen, $C_1$-$C_{20}$ alkyl group, $C_2$-$C_{20}$ alkenyl group, $C_6$-$C_{20}$ aryl group, $C_7$-$C_{20}$ alkylaryl group, $C_7$-$C_{20}$ arylalkyl group, $C_1$-$C_{20}$ alkoxy group, $C_2$-$C_{20}$ alkoxyalkyl group, $C_3$-$C_{20}$ heterocycloalkyl group, or $C_5$-$C_{20}$ heteroaryl group;

D is —O—, —S—, —N(R)—, or —Si(R)(R')—, wherein R and R' are same as or different from each other and each is independently hydrogen, halogen, $C_1$-$C_{20}$ alkyl group, $C_2$-$C_{20}$ alkenyl group, or $C_6$-$C_{20}$ aryl group;

L is $C_1$-$C_{10}$ linear or branched alkylene group;

B is carbon, silicon, or germanium;

Q is hydrogen, halogen, $C_1$-$C_{20}$ alkyl group, $C_2$-$C_{20}$ alkenyl group, $C_6$-$C_{20}$ aryl group, $C_7$-$C_{20}$ alkylaryl group, or $C_7$-$C_{20}$ arylalkyl group;

M is a Group 4 transition metal;

$X^1$ and $X^2$ are same as or different from each other and each is independently halogen, $C_1$-$C_{20}$ alkyl group, $C_2$-$C_{20}$ alkenyl group, $C_6$-$C_{20}$ aryl group, nitro group, amido group, $C_1$-$C_{20}$ alkylsilyl group, $C_1$-$C_{20}$ alkoxy group, or $C_1$-$C_{20}$ sulfonate group;

$C^1$ and $C^2$ are same as or different from each other and each is independently represented by any one of the following Chemical Formula 2a, Chemical Formula 2b or Chemical Formula 2c, provided that both $C^1$ and $C^2$ are not represented by the following Chemical Formula 2c:

[Chemical Formula 2a]

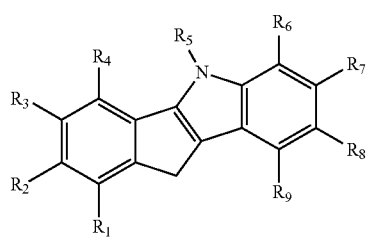

[Chemical Formula 2b]

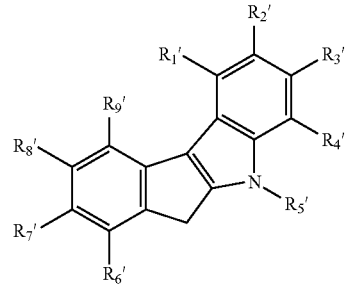

[Chemical Formula 2c]

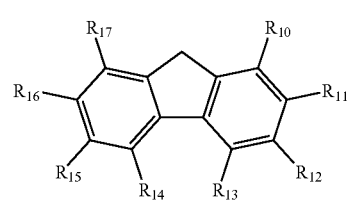

in Chemical Formulae 2a, 2b and 2c, $R_1$ to $R_{17}$ and $R_1'$ to $R_9'$ are same as or different from each other and each is independently hydrogen, halogen, $C_1$-$C_{20}$ alkyl group, $C_2$-$C_{20}$ alkenyl group, $C_1$-$C_{20}$ alkylsilyl group, $C_1$-$C_{20}$ silylalkyl group, $C_1$-$C_{20}$ alkoxysilyl group, $C_1$-$C_{20}$ alkoxy group, $C_6$-$C_{20}$ aryl group, $C_7$-$C_{20}$ alkylaryl group, or $C_7$-$C_{20}$ arylalkyl group, wherein two or more adjacent groups among $R_{10}$ to $R_{17}$ may be connected together to form substituted or unsubstituted aliphatic or aromatic ring;

$(CP^1R^a)(CP^2R^b)M^1Z^1_{3-n}$  [Chemical Formula 3]

in Chemical Formula 3, $M^1$ is a Group 4 transition metal;

$Cp^1$ and $Cp^2$ are same as or different from each other, and each independently any one selected from the group consisting of cyclopentadienyl, indenyl, 4,5,6,7-tetrahydro-1-indenyl, and fluorenyl radical, each of which may be substituted by hydrocarbon having 1 to 20 carbon atoms;

$R^a$ and $R^b$ are same as or different from each other, and each independently hydrogen, $C_1$-$C_{20}$ alkyl, $C_1$-$C_{10}$ alkoxy, $C_2$-$C_{20}$ alkoxyalkyl, $C_6$-$C_{20}$ aryl, $C_6$-$C_{10}$ aryloxy, $C_2$-$C_{20}$ alkenyl, $C_7$-$C_{40}$ alkylaryl, $C_7$-$C_{40}$ arylalkyl, $C_8$-$C_{40}$ arylalkenyl, or $C_2$-$C_{10}$ alkinyl;

$Z^1$ is halogen atom, $C_1$-$C_{20}$ alkyl, $C_2$-$C_{10}$ alkenyl, $C_7$-$C_{40}$ alkylaryl, $C_7$-$C_{40}$ arylalkyl, $C_6$-$C_{20}$ aryl, substituted or unsubstituted $C_1$-$C_{20}$ alkylidene, substituted or unsubstituted amino group, $C_2$-$C_{20}$ alkylalkoxy, or $C_7$-$C_{40}$ arylalkoxy; and n is 1 or 0;

$(Cp^3R^c)_mB^1(Cp^4R^d)M^2Z^2_{3-m}$ 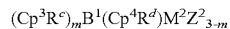 [Chemical Formula 4]

in Chemical Formula 4, $M^2$ is a Group 4 transition metal;

$Cp^3$ and $Cp^4$ are same as or different from each other, and each independently any one selected from the group consisting of cyclopentadienyl, indenyl, 4,5,6,7-tetrahydro-1-indenyl and fluorenyl radical, each of which may be substituted by hydrocarbon having 1 to 20 carbon atoms;

$R^c$ and $R^d$ are same as or different from each other, and each independently hydrogen, $C_1$-$C_{20}$ alkyl, $C_1$-$C_{10}$ alkoxy, $C_2$-$C_{20}$ alkoxyalkyl, $C_6$-$C_{20}$ aryl, $C_6$-$C_{10}$ aryloxy, $C_2$-$C_{20}$ alkenyl, $C_7$-$C_{40}$ alkylaryl, $C_7$-$C_{40}$ arylalkyl, $C_8$-$C_{40}$ arylalkenyl, or $C_2$-$C_{10}$ alkinyl;

$Z^2$ is halogen atom, $C_1$-$C_{20}$ alkyl, $C_2$-$C_{10}$ alkenyl, $C_7$-$C_{40}$ alkylaryl, $C_7$-$C_{40}$ arylalkyl, $C_6$-$C_{20}$ aryl, substituted or unsubstituted $C_1$-$C_{20}$ alkylidene, substituted or unsubstituted amino group, $C_2$-$C_{20}$ alkylalkoxy, or $C_7$-$C_{40}$ arylalkoxy;

$B^1$ is one or more selected among the radicals containing carbon, germanium, silicon, phosphorous or nitrogen atom, which crosslink $Cp^3R^c$ ring to $Cp^4R^d$ ring, or crosslink one $Cp^4R^d$ ring to $M^2$, or combinations thereof, and m is 1 or 0;

$(Cp^5R^e)B^2(J)M^3Z^3_2$     [Chemical Formula 5]

in Chemical Formula 5, $M^3$ is a Group 4 transition metal;

$Cp^5$ is any one selected from the group consisting of cyclopentadienyl, indenyl, 4,5,6,7-tetrahydro-1-indenyl and fluorenyl radical, each of which may be substituted by hydrocarbon having 1 to 20 carbon atoms;

$R^e$ is hydrogen, $C_1$-$C_{20}$ alkyl, $C_1$-$C_{10}$ alkoxy, $C_2$-$C_{20}$ alkoxyalkyl, $C_6$-$C_{20}$ aryl, $C_6$-$C_{10}$ aryloxy, $C_2$-$C_{20}$ alkenyl, $C_7$-$C_{40}$ alkylaryl, $C_7$-$C_{40}$ arylalkyl, $C_8$-$C_{40}$ arylalkenyl, or $C_2$-$C_{10}$ alkinyl;

$Z^3$ is halogen atom, $C_1$-$C_{20}$ alkyl, $C_2$-$C_{10}$ alkenyl, $C_7$-$C_{40}$ alkylaryl, $C_7$-$C_{40}$ arylalkyl, $C_6$-$C_{20}$ aryl, substituted or unsubstituted $C_1$-$C_{20}$ alkylidene, substituted or unsubstituted amino group, $C_2$-$C_{20}$ alkylalkoxy, or $C_7$-$C_{40}$ arylalkoxy;

$B^2$ is one or more selected among the radicals containing carbon, germanium, silicon, phosphorous or nitrogen atom, which crosslink $Cp^5R^e$ ring to J, or combinations thereof; and J is any one selected from the group consisting of $NR^f$, O, $PR^f$ and S, wherein $R^f$ is $C_1$-$C_{20}$ alkyl, aryl, substituted alkyl or substituted aryl.

In the hybrid supported metallocene catalyst according to the present invention, the substituents of Chemical Formulae 1, 3, 4 and 5 will be more specifically explained as follows.

The $C_1$-$C_{20}$ alkyl group may include a linear or branched alkyl group, and specific example thereof may include methyl group, ethyl group, propyl group, isopropyl group, n-butyl group, tert-butyl group, pentyl group, hexyl group, heptyl group, octyl group, and the like, however, it is not limited thereto.

The $C_2$-$C_{20}$ alkenyl group may include a linear or branched alkenyl group, and specifically, it may be allyl group, ethenyl group, propenyl group, butenyl group, pentenyl group, and the like, but is not limited thereto.

The $C_6$-$C_{20}$ aryl group may include a single ring aryl group or a condensed ring aryl group, and specific example thereof may include phenyl group, biphenyl group, naphthyl group, phenanthrenyl group, fluorenyl group, and the like, but is not limited thereto.

The $C_5$-$C_{20}$ heteroaryl group may include a single ring heteroaryl group or a condensed ring heteroaryl group, and specific example thereof may include carbazolyl group, pyridyl group, quinoline group, isoquinoline group, thiophenyl group, furanyl group, imidazole group, oxazolyl group, thiazolyl group, triazine group, tetrahydropyranyl group, tetrahydrofuranyl group, and the like, but is not limited thereto.

The $C_1$-$C_{20}$ alkoxy group may include methoxy group, ethoxy group, phenyloxy group, cyclohexyloxy group, and the like, but is not limited thereto.

The Group 4 transition metal may include titanium, zirconium, hafnium, and the like, but is not limited thereto.

In the hybrid supported metallocene catalyst according to the present invention, it is more preferable that $R_1$ to $R_{17}$ and $R_1'$ to $R_9'$ in Chemical Formulae 2a, 2b and 2c are each independently hydrogen, methyl group, ethyl group, propyl group, isopropyl group, n-butyl group, tert-butyl group, pentyl group, hexyl group, heptyl group, octyl group, phenyl group, halogen group, trimethylsilyl group, triethylsilyl group, tripropylsilyl group, tributylsilyl group, triisopropylsilyl group, trimethylsilylmethyl group, methoxy group, or ethoxy group, however, it is not limited thereto.

It is more preferable that L in Chemical Formula 1 is a linear or branched $C_4$-$C_8$ alkylene group, however, it is not limited thereto. Furthermore, the alkylene group may be unsubstituted or substituted by $C_1$-$C_{20}$ alkyl group, $C_2$-$C_{20}$ alkenyl group, or $C_6$-$C_{20}$ aryl group.

Also, it is preferable that A in Chemical Formula 1 is hydrogen, methyl group, ethyl group, propyl group, isopropyl group, n-butyl group, tert-butyl group, methoxymethyl group, tert-butoxymethyl group, 1-ethoxyethyl group, 1-methyl-1-methoxyethyl group, tetrahydropyranyl group, or tetrahydrofuranyl group, however, it is not limited thereto.

Also, it is preferable that B in Chemical Formula 1 is silicon, however, it is not limited thereto.

Because the first metallocene compound of Chemical Formula 1 includes a structure in which an indenoindole derivative and/or a fluorene derivative are crosslinked via a bridge and has an unshared electron pair capable of acting as a Lewis base in the ligand structure, it is supported on the surface of a support having a Lewis acid character to show a high polymerization activity even when supported. Furthermore, it is superior in activity because of including the electron-rich indenoindole group and/or fluorene group. In addition, due to a proper steric hindrance and an electronic effect of the ligand, it is low in hydrogen reactivity and also maintains a high activity even in the presence of hydrogen. Further, it can be used for preparing an olefinic polymer of ultra-high molecular weight because nitrogen atom of the indenoindole derivative stabilizes the beta-hydrogen of growing polymer chain with a hydrogen bond and inhibits beta-hydrogen elimination.

According to one embodiment of the present invention, specific examples of the compound represented by Chemical Formula 2a may include one of the compounds represented by the following structural formulae, however, it is not limited thereto:

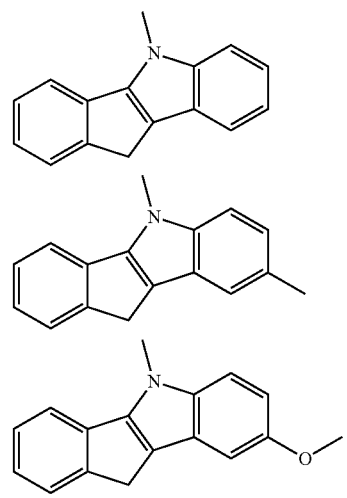

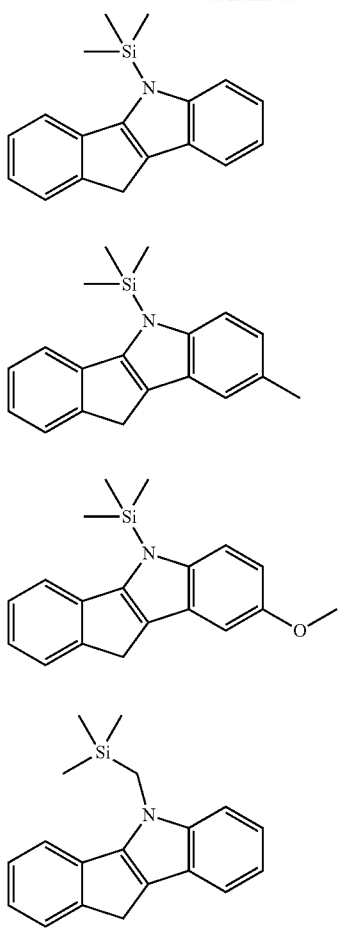
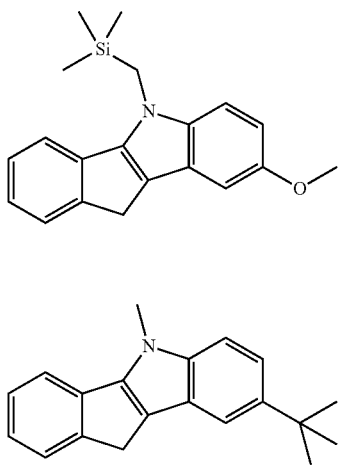
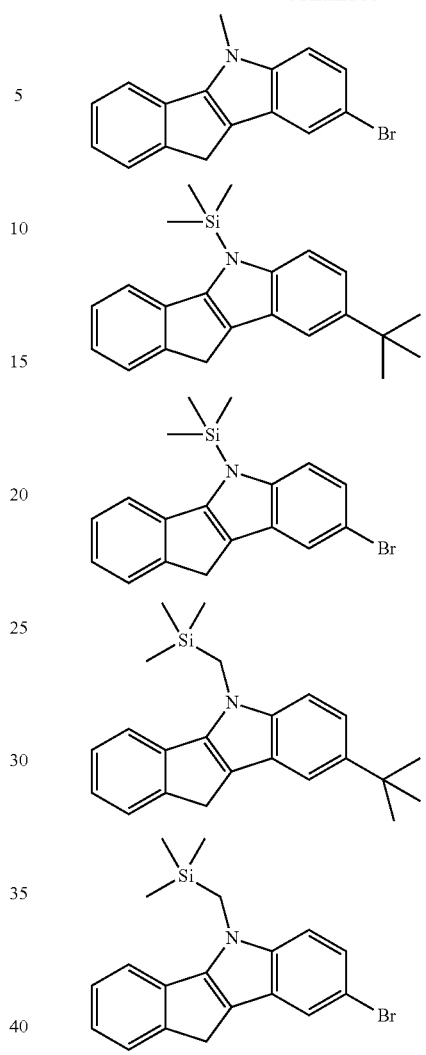
According to one embodiment of the present invention, specific examples of the compound represented by Chemical Formula 2b may include one of the compounds represented by the following structural formulae, however, it is not limited thereto:
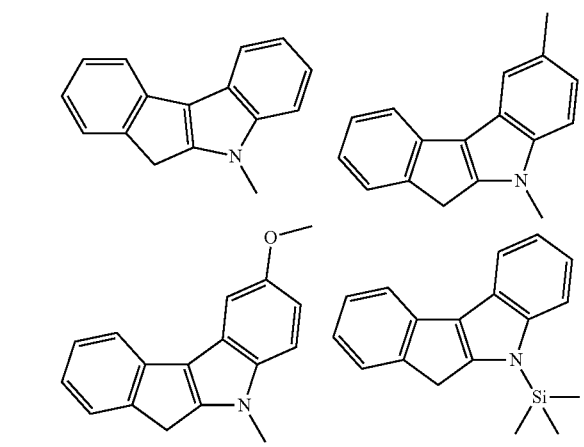

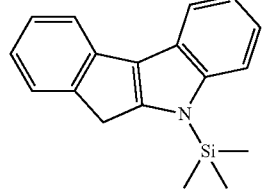
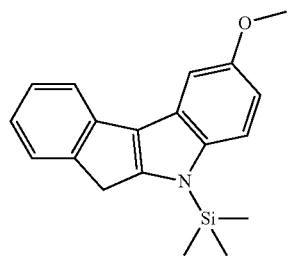
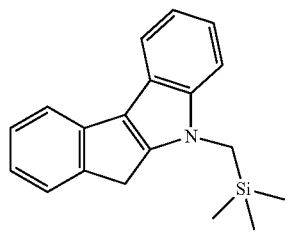
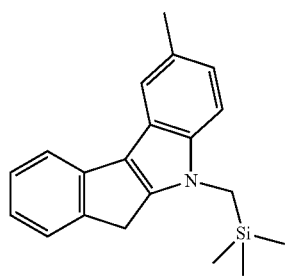
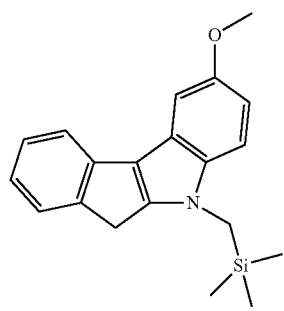
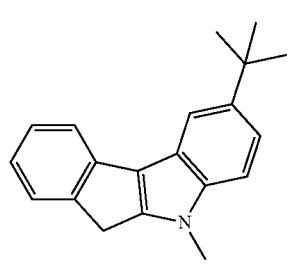
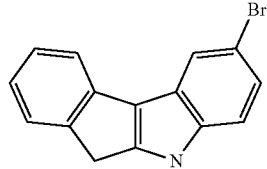
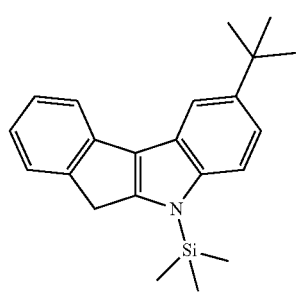
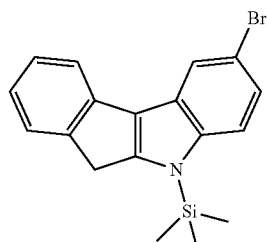
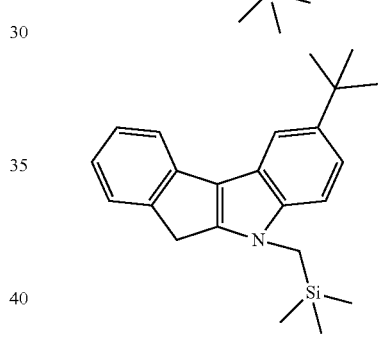
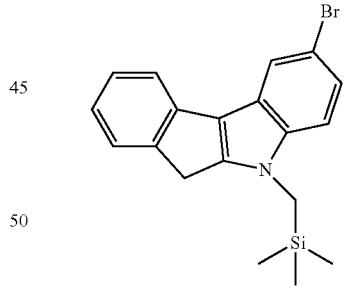
According to one embodiment of the present invention, specific examples of the compound represented by Chemical Formula 2c may include one of the compounds represented by the following structural formulae, however, it is not limited thereto:
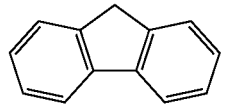

-continued
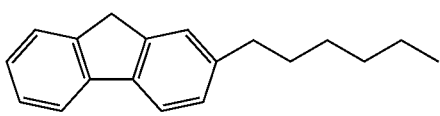
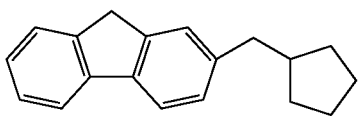
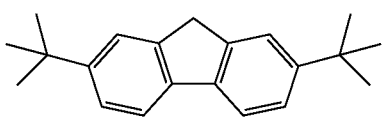
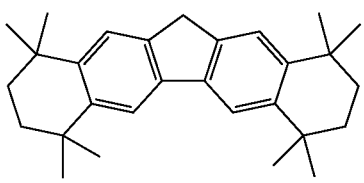
According to one embodiment of the present invention, specific examples of the first metallocene compound represented by Chemical Formula 1 may be one of the compounds represented by the following structural formulae, however, it is not limited thereto:
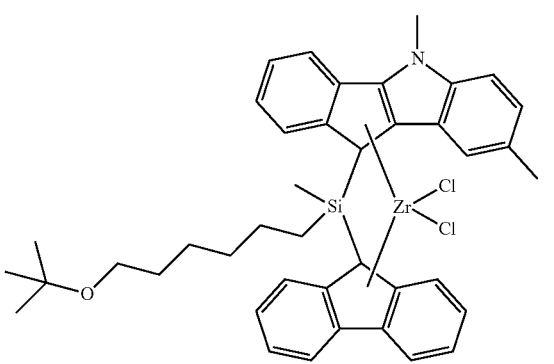
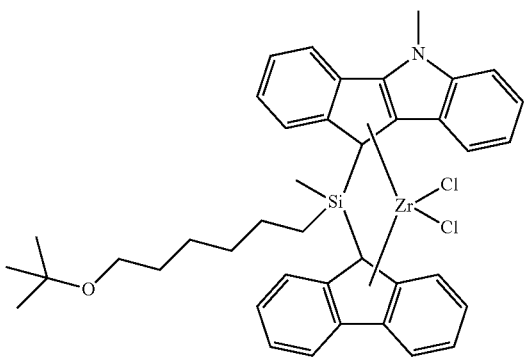
-continued
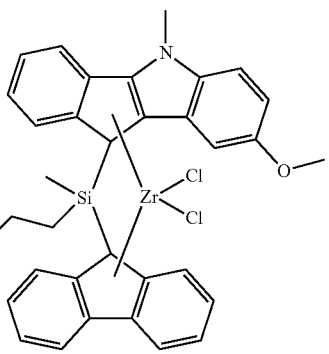
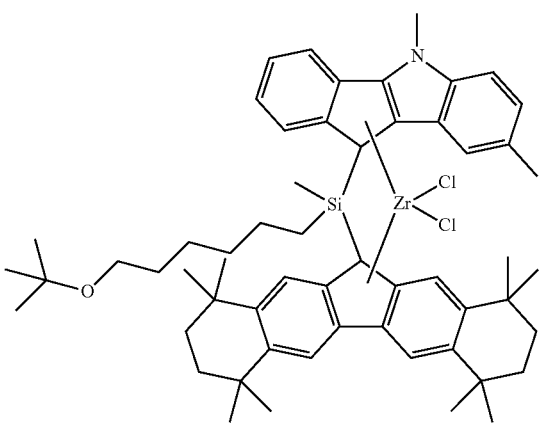
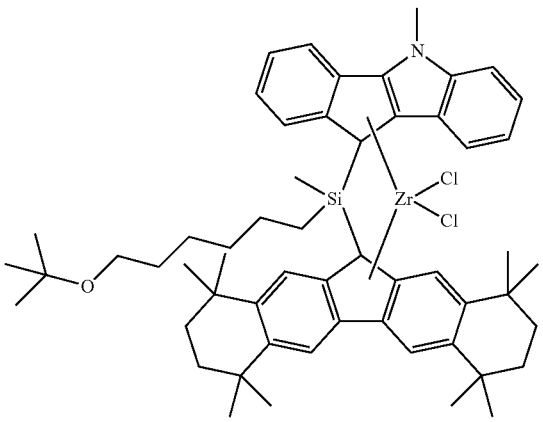
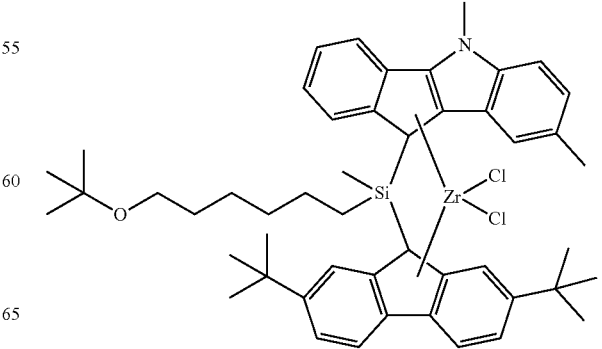

-continued
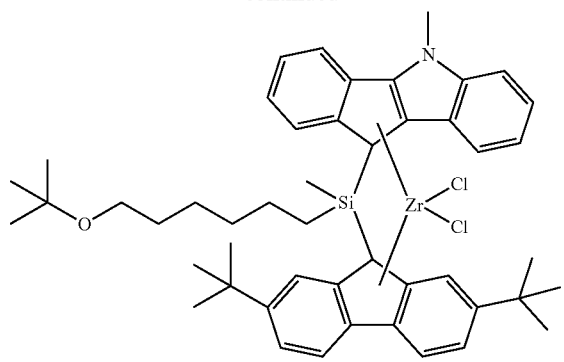
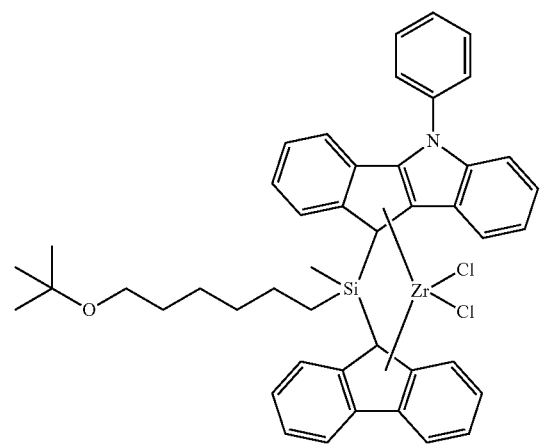
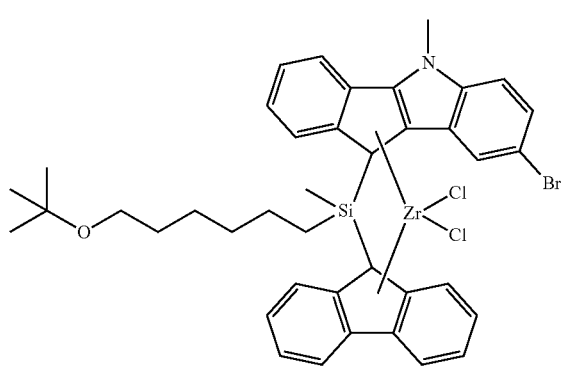
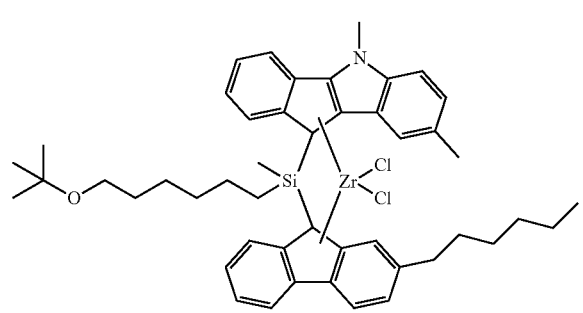
-continued
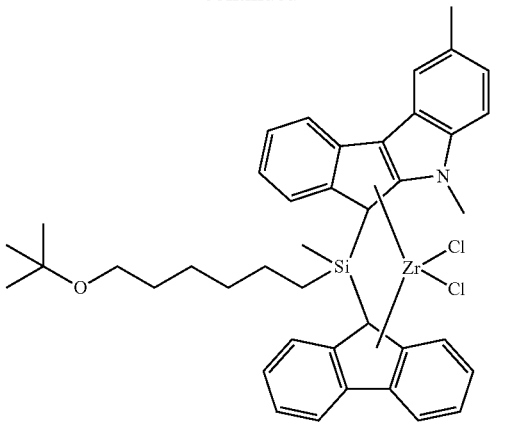
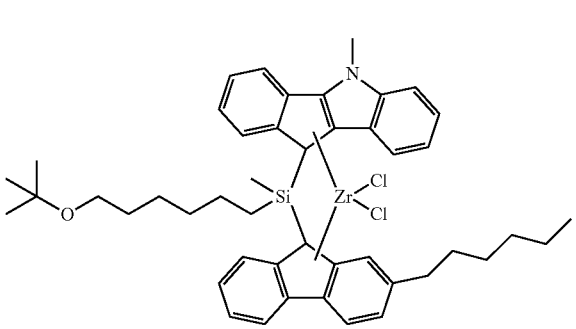
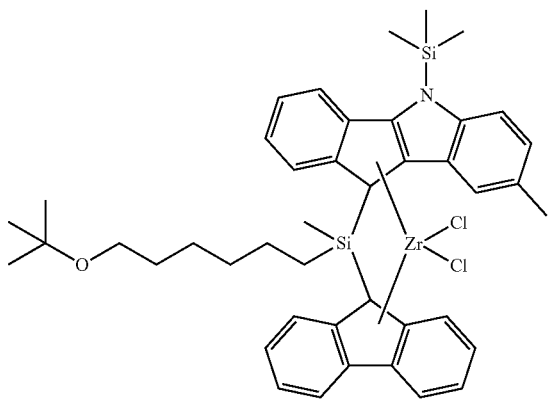
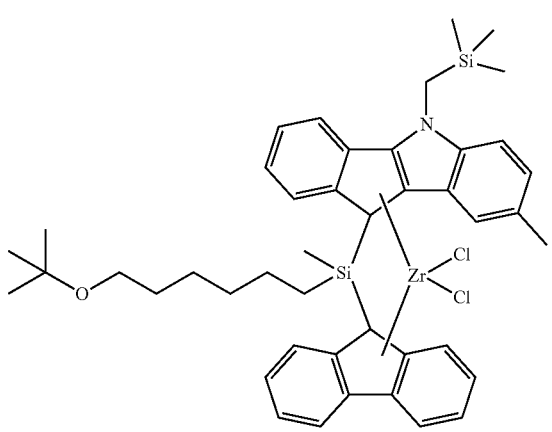

15
-continued

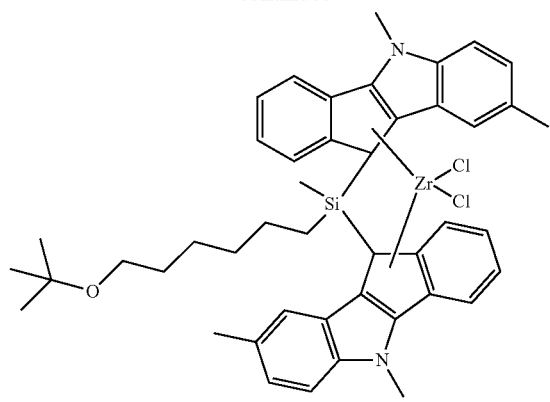

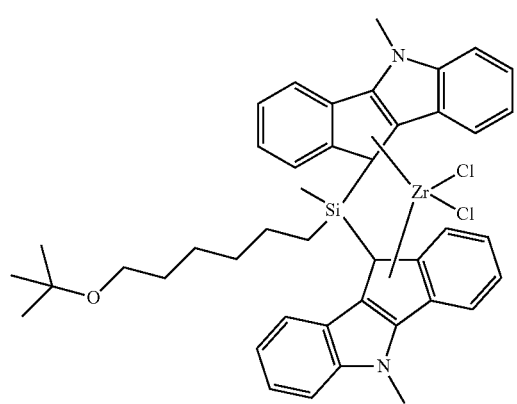

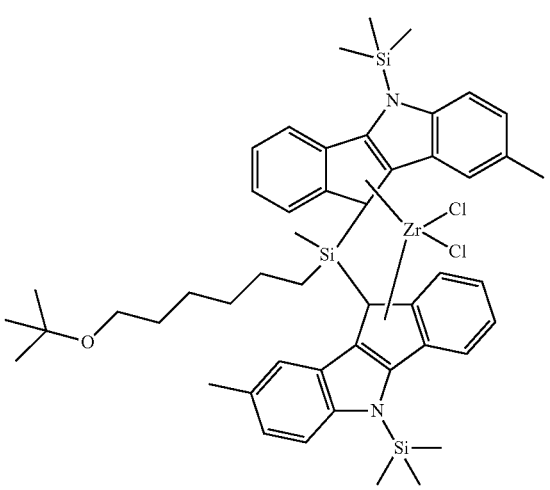

16
-continued

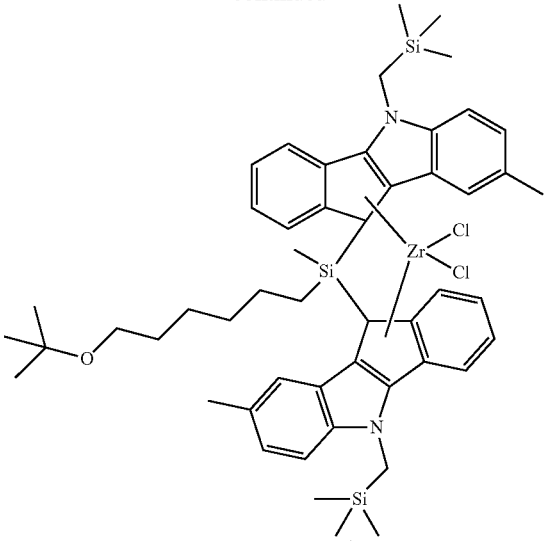

The first metallocene compound of Chemical Formula 1 has a superior activity, and can polymerize an olefinic polymer having high molecular weight. In particular, it can show a high polymerization activity even when it is used in the state of being supported on a support. Therefore, it can prepare a polyolefinic polymer of ultra-high molecular weight.

Also, even when the polymerization reaction is carried out in the presence of hydrogen in order to prepare an olefinic polymer having high molecular weight and broad molecular weight distribution at the same time, the first metallocene compound of Chemical Formula 1 according to the present invention shows a low hydrogen reactivity and thus can polymerize an olefinic polymer of ultra-high molecular weight still with a high activity. Therefore, even when it is used as a hybrid with a catalyst having different characteristics, it can prepare an olefinic polymer satisfying the characteristics of high molecular weight without lowering of its activity, resulting in the easy preparation of an olefinic polymer containing the olefinic polymer having high molecular weight and broad molecular weight distribution together.

The first metallocene compound of Chemical Formula 1 may be obtained by connecting an indenoindole derivative and/or a fluorene derivative via a bridge compound to prepare a ligand compound, and then introducing a metal precursor compound therein to perform a metallation. The method for preparing the first metallocene compound will be specifically explained in the examples to be described below.

In the hybrid supported metallocene catalyst according to the present invention, the second metallocene compound may be one or more selected among the compounds of Chemical Formulae 3 to 5:

(Cp$^1$R$^a$)(Cp$^2$R$^b$)M$^1$Z$^1_{3-n}$  [Chemical Formula 3]

in Chemical Formula 3,

M$^1$ is a Group 4 transition metal;

Cp$^1$ and Cp$^2$ are same as or different from each other and are each independently any one selected from the group consisting of cyclopentadienyl, indenyl, 4,5,6,7-tetrahydro-1-indenyl, and fluorenyl radical, each of which may be substituted by hydrocarbon having 1 to 20 carbon atoms;

R$^a$ and R$^b$ are same as or different from each other and are each independently hydrogen, C$_1$-C$_{20}$ alkyl, C$_1$-C$_{10}$ alkoxy, C$_2$-C$_{20}$ alkoxyalkyl, C$_6$-C$_{20}$ aryl, C$_6$-C$_{10}$ aryloxy, C$_2$-C$_{20}$ alkenyl, C$_7$-C$_{40}$ alkylaryl, C$_7$-C$_{40}$ arylalkyl, C$_8$-C$_{40}$ arylalkenyl, or C$_2$-C$_{10}$ alkinyl;

Z$^1$ is halogen atom, C$_1$-C$_{20}$ alkyl, C$_2$-C$_{10}$ alkenyl, C$_7$-C$_{40}$ alkylaryl, C$_7$-C$_{40}$ arylalkyl, C$_6$-C$_{20}$ aryl, substituted or unsubstituted C$_1$-C$_{20}$ alkylidene, substituted or unsubstituted amino group, C$_2$-C$_{20}$ alkylalkoxy, or C$_7$-C$_{40}$ arylalkoxy; and n is 1 or 0;

(Cp$^3$R$^c$)$_m$B$_1$(Cp$^4$R$^d$)M$^2$Z$^2_{3-m}$  [Chemical Formula 4]

in Chemical Formula 4,

M$^2$ is a Group 4 transition metal;

Cp$^3$ and Cp$^4$ are same as or different from each other, and each independently any one selected from the group consisting of cyclopentadienyl, indenyl, 4,5,6,7-tetrahydro-1-indenyl and fluorenyl radical, each of which may be substituted by hydrocarbon having 1 to 20 carbon atoms;

R$^c$ and R$^d$ are same as or different from each other, and each independently hydrogen, C$_1$-C$_{20}$ alkyl, C$_1$-C$_{10}$ alkoxy, C$_2$-C$_{20}$ alkoxyalkyl, C$_6$-C$_{20}$ aryl, C$_6$-C$_{10}$ aryloxy, C$_2$-C$_{20}$ alkenyl, C$_7$-C$_{40}$ alkylaryl, C$_7$-C$_{40}$ arylalkyl, C$_8$-C$_{40}$ arylalkenyl, or C$_2$-C$_{10}$ alkinyl;

Z$^2$ is halogen atom, C$_1$-C$_{20}$ alkyl, C$_2$-C$_{10}$ alkenyl, C$_7$-C$_{40}$ alkylaryl, C$_7$-C$_{40}$ arylalkyl, C$_6$-C$_{20}$ aryl, substituted or unsubstituted C$_1$-C$_{20}$ alkylidene, substituted or unsubstituted amino group, C$_2$-C$_{20}$ alkylalkoxy, or C$_7$-C$_{40}$ arylalkoxy;

B$^1$ is one or more selected among the radicals containing carbon, germanium, silicon, phosphorous or nitrogen atom, which crosslink Cp$^3$R$^c$ ring to Cp$^4$R$^d$ ring or crosslink one Cp$^4$R$^d$ ring to M$^2$, or combinations thereof; and m is 1 or 0;

(Cp$^5$R$^e$)B$^2$(J)M$^3$Z$^3_2$  [Chemical Formula 5]

in Chemical Formula 5,

M$^3$ is a Group 4 transition metal;

Cp$^5$ is any one selected from the group consisting of cyclopentadienyl, indenyl, 4,5,6,7-tetrahydro-1-indenyl and fluorenyl radical, each of which may be substituted by hydrocarbon having 1 to 20 carbon atoms;

R$^e$ is hydrogen, C$_1$-C$_{20}$ alkyl, C$_1$-C$_{10}$ alkoxy, C$_2$-C$_{20}$ alkoxyalkyl, C$_6$-C$_{20}$ aryl, C$_6$-C$_{10}$ aryloxy, C$_2$-C$_{20}$ alkenyl, C$_7$-C$_{40}$ alkylaryl, C$_7$-C$_{40}$ arylalkyl, C$_8$-C$_{40}$ arylalkenyl, or C$_2$-C$_{10}$ alkinyl;

Z$^3$ is halogen atom, C$_1$-C$_{20}$ alkyl, C$_2$-C$_{10}$ alkenyl, C$_7$-C$_{40}$ alkylaryl, C$_7$-C$_{40}$ arylalkyl, C$_6$-C$_{20}$ aryl, substituted or unsubstituted C$_1$-C$_{20}$ alkylidene, substituted or unsubstituted amino group, C$_2$-C$_{20}$ alkylalkoxy, or C$_7$-C$_{40}$ arylalkoxy;

B$^2$ is one or more selected among the radicals containing carbon, germanium, silicon, phosphorous or nitrogen atom, which crosslink Cp$^5$R$^e$ ring to J, or combinations thereof and J is any one selected from the group consisting of NR$^f$, O, PR$^f$ and S, wherein R$^f$ is C$_1$-C$_{20}$ alkyl, aryl, substituted alkyl or substituted aryl.

In Chemical Formula 4, when m is 1, it means a bridge compound structure wherein Cp$^3$R$^c$ ring and Cp$^4$R$^d$ ring or Cp$^4$R$^d$ ring and M$^2$ are crosslinked via B$^1$. When m is 0, it means a non-crosslinked compound structure.

The specific example of the compound represented by Chemical Formula 3 may be one of the compounds represented by the following structural formulae, however, it is not limited to thereto:

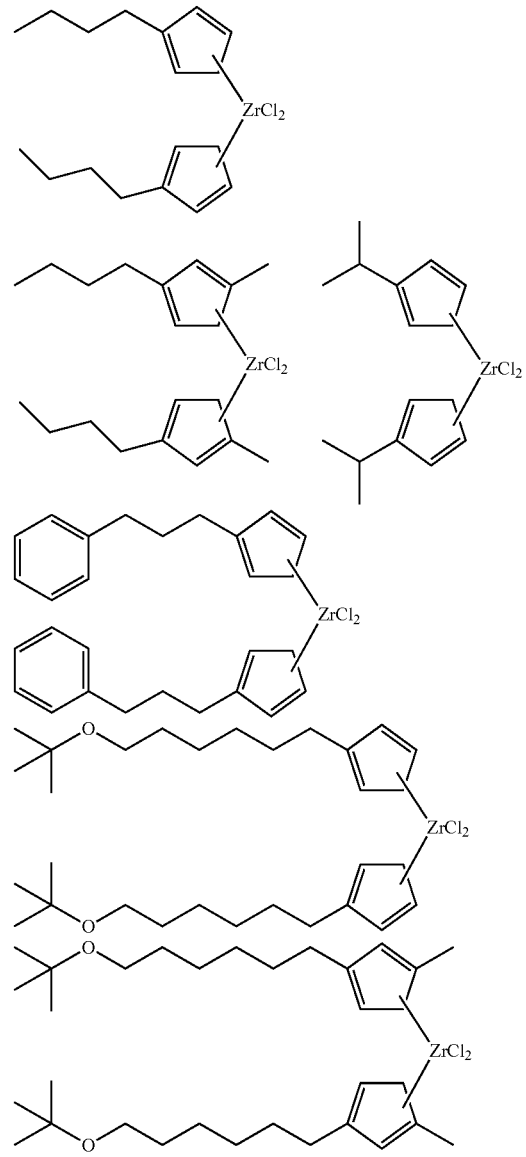

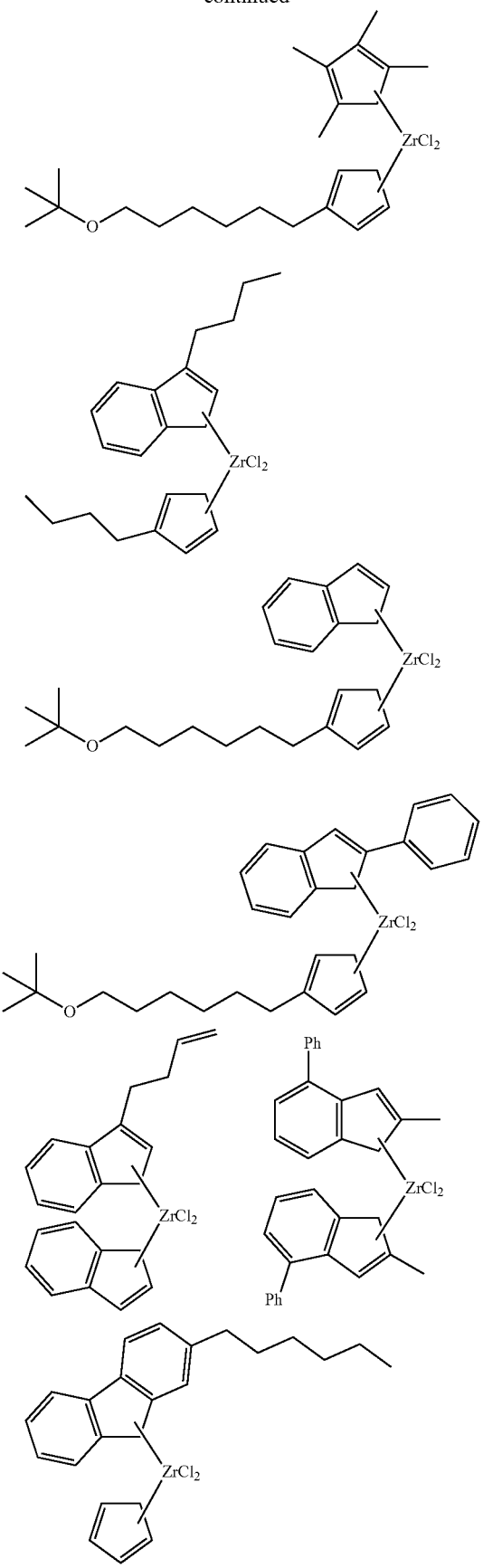
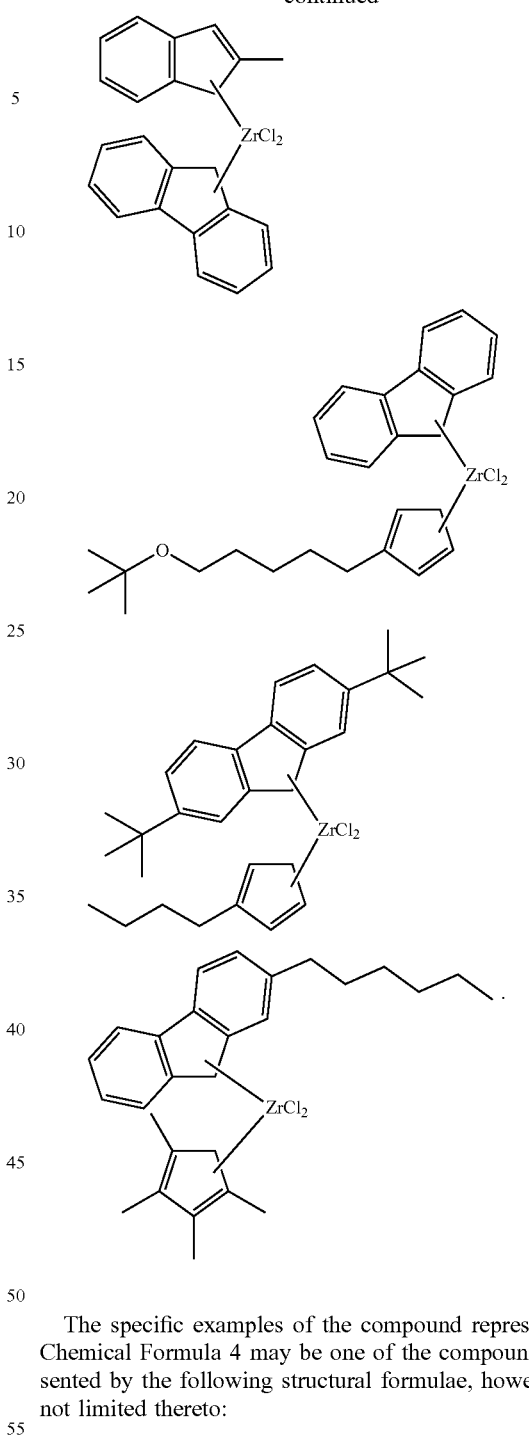
The specific examples of the compound represented by Chemical Formula 4 may be one of the compounds represented by the following structural formulae, however, it is not limited thereto:
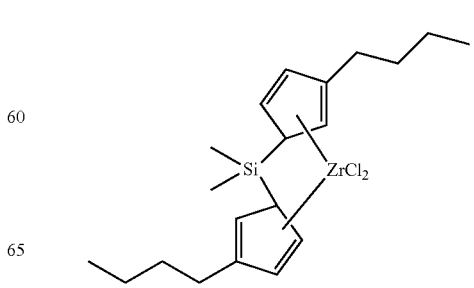

-continued
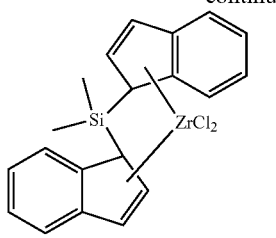
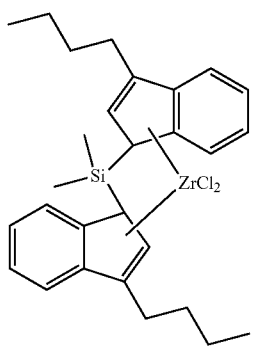
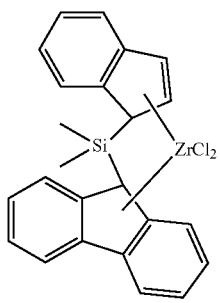
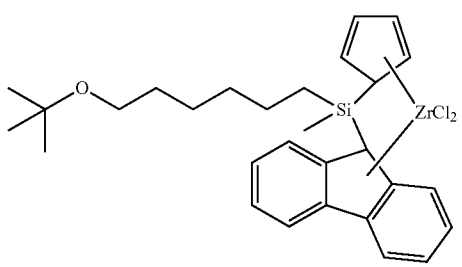
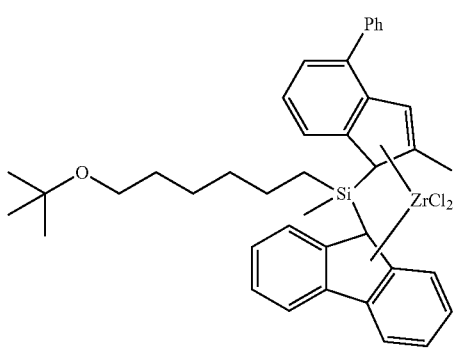
-continued
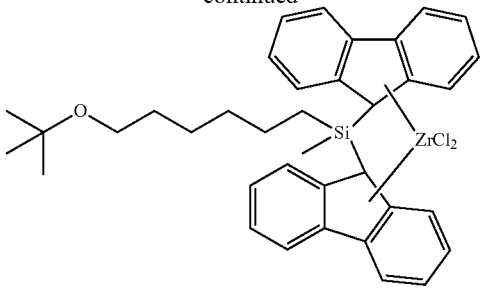
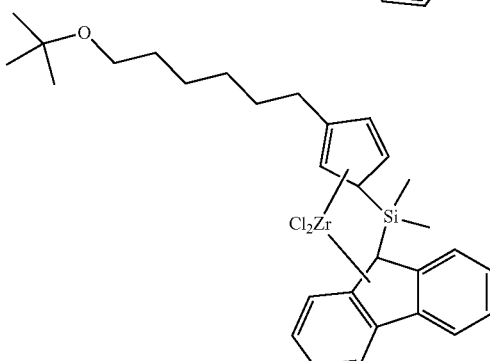
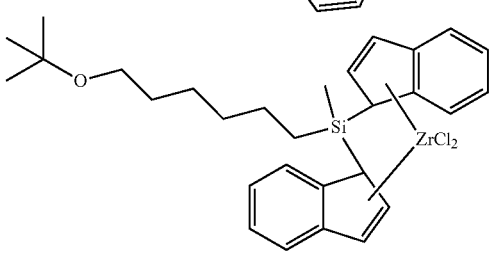
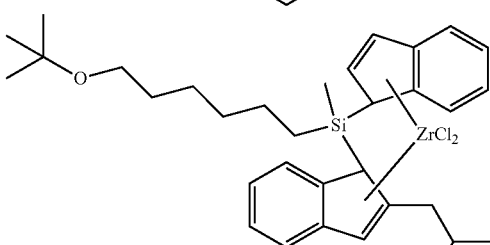
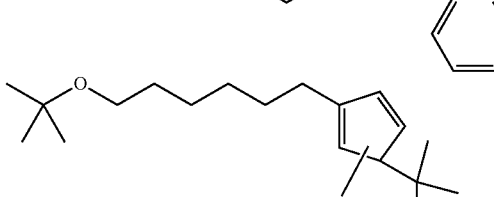
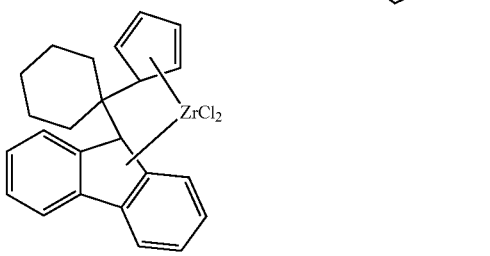

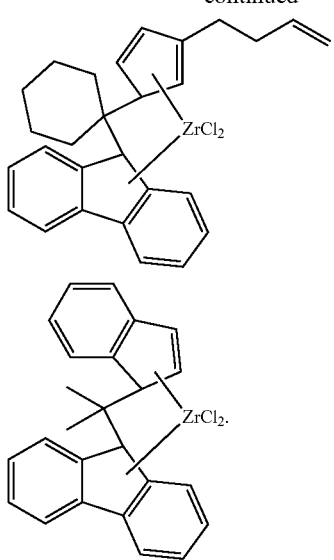

Also, specific examples of the compound represented by Chemical Formula 5 may be one of the compounds represented by the following structural formulae, however, it is not limited thereto:

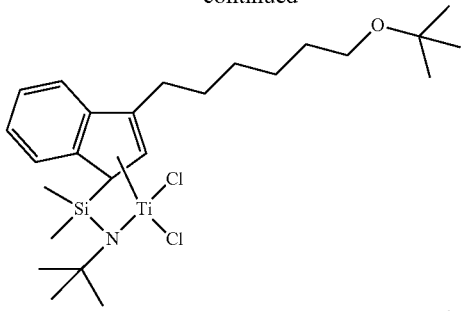
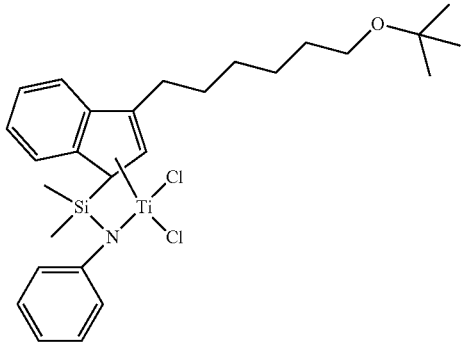
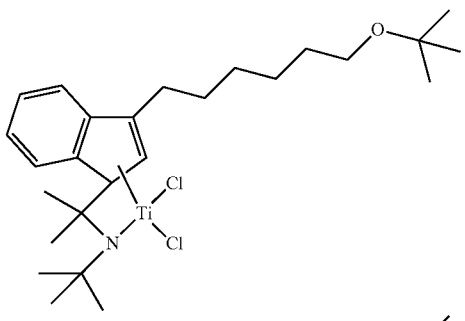
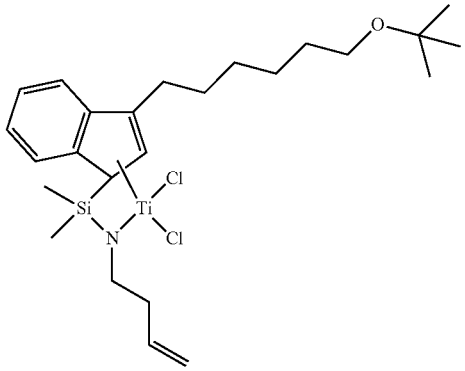
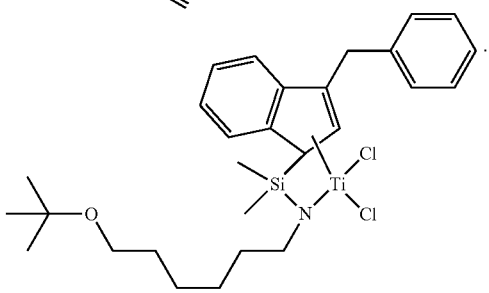

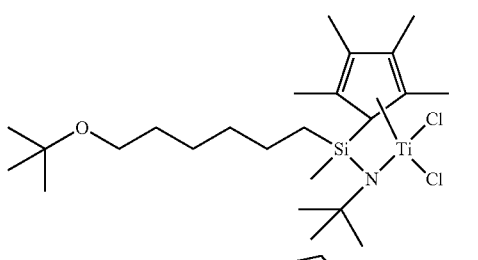
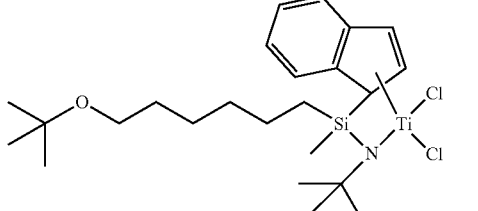
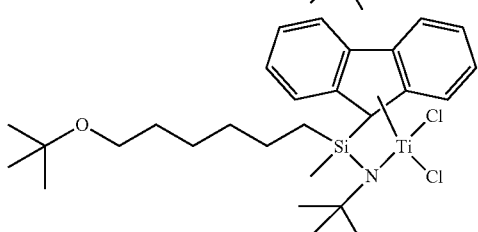
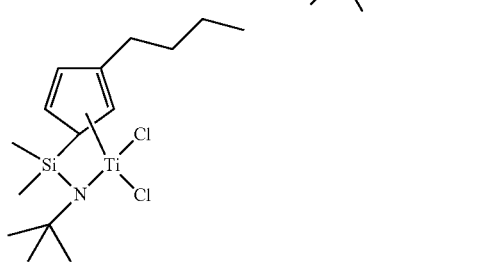

The hybrid supported metallocene catalyst according to the present invention is prepared by supporting one or more first metallocene compounds represented by Chemical Formula 1 and one or more second metallocene compounds selected among the compounds represented by Chemical Formula 3 to Chemical Formula 5 on a support with a cocatalyst compound.

In the above-described hybrid supported metallocene catalyst, the first metallocene compound represented by Chemical Formula 1 may mainly contribute to prepare copolymers having high molecular weight and high SCB (short chain branch) content, and the second metallocene compound represented by Chemical Formula 3 may mainly contribute to prepare copolymers having low molecular weight and low SCB content. Also, the second metallocene compound represented by Chemical Formula 4 or Chemical Formula 5 may contribute to prepare copolymers having low molecular weight and medium SCB content.

According to one embodiment of the present invention, the hybrid supported metallocene catalyst may include one or more first metallocene compounds represented by Chemical Formula 1 and one or more second metallocene compounds represented by Chemical Formula 3.

According to another embodiment of the present invention, the hybrid supported metallocene catalyst may include one or more second metallocene compounds represented by Chemical Formula 4 or Chemical Formula 5, in addition to one or more first metallocene compounds represented by Chemical Formula 1 and one or more second metallocene compounds represented by Chemical Formula 3.

In the hybrid supported metallocene catalyst according to the present invention, since the first metallocene compound forms a ligand structure in which an indenoindole derivative and a fluorene derivative are crosslinked via a bridge compound and has an unshared electron pair capable of acting as a Lewis base in the ligand structure, it is supported on the surface of a support having a Lewis acid character to show a high polymerization activity even when supported. Furthermore, it is superior in activity because of including the electron-rich indenoindole group and/or fluorene group. In addition, due to a proper steric hindrance and an electronic effect of the ligand, it is low in hydrogen reactivity and also maintains a high activity even in the presence of hydrogen. Therefore, when a hybrid supported metallocene catalyst is prepared using such a transition metal compound, an olefinic polymer of ultra-high molecular weight can be obtained because nitrogen atom of the indenoindole derivative stabilizes the beta-hydrogen of growing polymer chain with a hydrogen bond.

Also, the hybrid supported metallocene catalyst of the present invention includes the first metallocene compound represented by Chemical Formula 1 and the second metallocene compound selected among the compounds represented by Chemical Formula 3 to Chemical Formula 5. Thus, as the hybrid supported metallocene catalyst includes two or more different types of the metallocene compounds, it is possible to prepare not only an olefinic copolymer having high SCB content and high molecular weight but also an olefinic copolymer having excellent physical property and workability due to its broad molecular weight distribution.

In the hybrid supported metallocene catalyst according to the present invention, the cocatalyst which is supported together on a support to activate the metallocene compound is an organic metal compound containing a Group 13 metal. The cocatalyst compound is not particularly limited as long as it can be used for the polymerization of olefin in the presence of a typical metallocene catalyst.

Specifically, the cocatalyst compound may comprise one or more of the first aluminum-containing cocatalyst represented by the following Chemical Formula 6 and the second borate-based cocatalyst represented by the following Chemical Formula 7:

—[Al($R_{18}$)—O—]$_k$—     [Chemical Formula 6]

in Chemical Formula 6, each of $R_{18}$ is independently halogen, or unsubstituted or halogen-substituted hydrocarbyl group having 1 to 20 carbon atoms; and k is an integer of 2 or more, $T^+[BG_4]^-$     [Chemical Formula 7]

in Chemical Formula 7, $T^+$ is a monovalent polyatomic ion. B is boron in an oxidation state of +3, and each of G is independently selected from the group consisting of hydride group, dialkylamido group, halide group, alkoxide group, aryloxide group, hydrocarbyl group, halocarbyl group and halo-substituted hydrocarbyl group, wherein G has less than 20 carbon atoms, provided that G is halide group at one or less position.

Using the first and the second cocatalysts as above, the polyolefins finally prepared may have more uniform molecular weight distribution, while the polymerization activity can be enhanced.

The first cocatalyst represented by Chemical Formula 6 may be an alkylaluminoxane-based compound wherein the repeating units are combined into a linear, circular or network structure. Specific examples of the first cocatalyst include methylaluminoxane (MAO), ethylaluminoxane, isobutylaluminoxane, butylaluminoxane, and the like.

Also, the second cocatalyst represented by Chemical Formula 7 may be a borate-based compound in the form of a trisubstituted ammonium salt, a dialkyl ammonium salt, or a trisubstituted phosphonium salt. Specific examples of the second cocatalyst include a borate-based compound in the form of a trisubstituted ammonium salt such as trimethylammonium tetraphenylborate, methyldioctadecylammonium tetraphenylborate, triethylammonium tetraphenylborate, tripropylammonium tetraphenylborate, tri(n-butyl) ammonium tetraphenylborate, methyltetradecyclooctadecylammonium tetraphenylborate, N,N-dimethylanilium tetraphenylborate, N,N-diethylanilium tetraphenylborate, N,N-dimethyl(2,4,6-trimethylanilium)tetraphenylborate, trimethylammonium tetrakis(pentafluorophenyl)borate, methylditetradecylammonium tetrakis(pentaphenyl)borate, methyldioctadecylammonium tetrakis(pentafluorophenyl)borate, triethylammonium, tetrakis(pentafluorophenyl)borate, tripropylammoniumtetrakis(pentafluorophenyl)borate, tri(n-butyl)ammonium tetrakis(pentafluorophenyl)borate, tri(secondary-butyl) ammoniumtetrakis(pentafluorophenyl)borate, N,N-dimethylanilium tetrakis(pentafluorophenyl)borate, N,N-diethylaniliumtetrakis(pentafluorophenyl)borate, N,N-dimethyl(2,4,6-trimethylanilium)tetrakis (pentafluorophenyl)borate, trimethylammoniumtetrakis(2,3, 4,6-tetrafluorophenyl)borate, triethylammonium tetrakis(2, 3,4,6-tetrafluorophenyl)borate, tripropylammonium tetrakis (2,3,4,6-tetrafluorophenyl)borate, tri(n-butyl)ammonium tetrakis(2,3,4,6-,tetrafluorophenyl)borate, dimethyl(t-butyl) ammonium tetrakis(2,3,4,6-tetrafluorophenyl)borate, N,N-dimethylanilium tetrakis(2,3,4,6-tetrafluorophenyl)borate, N,N-diethylanilium tetrakis(2,3,4,6-tetrafluorophenyl)borate, N,N-dimethyl-(2,4,6-trimethylanilium)tetrakis-(2,3,4, 6-tetrafluorophenyl)borate, and the like; a borate-based compound in the form of a dialkylammonium salt such as dioctadecylammonium tetrakis(pentafluorophenyl)borate, ditetradecylammonium tetrakis(pentafluorophenyl)borate, dicyclohexylammonium tetrakis(pentafluorophenyl)borate, and the like; or a borate-based compound in the form of a trisubstituted phosphonium salt such as triphenylphosphonium tetrakis(pentafluorophenyl)borate, methyldioctadecylphosphonium tetrakis(pentafluorophenyl)borate or tri(2,6-dimethylphenyl)phosphonium tetrakis(pentafluorophenyl) borate, and the like.

In the hybrid supported metallocene catalyst according to the present invention, the weight ratio between the whole transition metals contained in the first metallocene compound represented by Chemical Formula 1 and the second metallocene compounds represented by Chemical Formulae 3 to 5 and the support may be 1:10 to 1:1.000. When the catalyst contains the support and the metallocene compounds in the above weight ratio, the optimum shape may be provided.

Also, the weight ratio of the cocatalyst compound to the support may be 1:1 to 1:100. Also, the weight ratio of the first metallocene compound represented by Chemical Formula 1 to the second metallocene compounds represented by Chemical Formulae 3 to 5 may be 10:1 to 1:10 and preferably 5:1 to 1:5. When the catalyst contains the cocatalyst and the metallocene compounds in the above ratio, it is possible to optimize the activity and the polymer microstructure.

In the hybrid supported metallocene catalyst according to the present invention, as the support, a support containing a hydroxyl group on its surface may be used, and preferably a support containing a highly reactive hydroxyl group and siloxane group, of which surface is dried to remove moisture, may be used.

For example, silica, silica-alumina, and silica-magnesia that are dried at a high temperature may be used, and they may usually contain oxides, carbonates, sulfates, and nitrates such as $Na_2O$, $K_2CO_3$, $BaSO_4$, $Mg(NO_3)_2$ or the like.

The support is preferably dried at 200 to 800° C., more preferably at 300 to 600° C., and most preferably at 300 to 400° C. If the drying temperature of the support is lower than 200° C. it retains moisture too much so that moisture on the surface is reacted with the cocatalyst. If the drying temperature is higher than 800° C., pores on the surface of the support are combined with each other to reduce surface area, and many hydroxyl groups are lost on the surface to remain only siloxane groups. Thus, since the reactive sites with cocatalyst are reduced, it is not preferable.

The amount of hydroxyl group on the surface of the support is preferably 0.1 to 10 mmol/g, and more preferably 0.5 to 5 mmol/g. The amount of hydroxyl group on the surface of the support may be controlled depending on the preparation method and conditions of the support, or drying conditions such as temperature, time, vacuum, spray drying, and the like.

If the amount of hydroxyl group is less than 0.1 mmol/g, the reactive sites with cocatalyst are reduced. If the amount of hydroxyl group is more than 10 mmol/g, it is not desirable because it may be caused by moisture besides the hydroxyl groups present on the surface of support particles.

The hybrid supported metallocene catalyst according to the present invention may be used for polymerization of olefinic monomer as it stands. Also, the hybrid supported metallocene catalyst according to the present invention may be prepared as a pre-polymerized catalyst by contacting the catalyst with an olefinic monomer. For example, it may be prepared as a pre-polymerized catalyst by contacting the catalyst with an olefinic monomer such as ethylene, propylene, 1-butene, 1-hexene, 1-octene, and the like.

The hybrid supported metallocene catalyst according to the present invention is prepared, for example, by a step of supporting a cocatalyst compound on a support; a step of supporting the first metallocene compound represented by Chemical Formula 1 on the support; and a step of supporting the second cocatalyst compound selected among the compounds represented by Chemical Formulae 3 to 5 on the support.

In the method of preparing the hybrid supported metallocene catalyst as described above, the order of performing the step of supporting the first metallocene compound and the step of supporting the second metallocene compound may be varied as needed. In other words, after supporting the first metallocene compound on the support first, the second metallocene compound may be additionally supported to prepare the hybrid supported metallocene catalyst. Alternatively, after supporting the second metallocene compound on the support first, the first metallocene compound may be additionally supported to prepare the hybrid supported metallocene catalyst.

The process for preparing the hybrid supported metallocene catalyst as above may be carried out at a temperature of about 0 to about 100° C. (under normal pressure, but is not limited thereto. The olefinic polymer can be prepared by polymerizing olefinic monomer in the presence of the hybrid supported metallocene catalyst according to the present invention.

The olefinic monomer may include ethylene, alpha-olefin, cyclic olefin, diene olefin or triene olefin having two or more double bonds.

Specific examples of the olefinic monomer include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, norbornene, norbornadiene, ethylidenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, 3-chloromethylstyrene, and the like, and it is also possible to copolymerize by mixing two or more monomers thereof.

The polymerization reaction may be carried out by homopolymerizing one type of olefinic monomer or copolymerizing two types or more of monomers, using a continuous slurry polymerization reactor, a loop slurry reactor, a gas phase reactor, or a solution reactor.

The hybrid supported metallocene catalyst can be used after being dissolved or diluted in an aliphatic hydrocarbon solvent having 5 to 12 carbon atoms such as pentane, hexane, heptane, nonane, decane, and isomers thereof, an aromatic hydrocarbon solvent such as toluene and benzene, or a hydrocarbon solvent substituted with chlorine atom such as dichloromethane and chlorobenzene. It is preferable that the solvent is used after a small amount of water, air or the like acting as a catalyst poison is removed by treating with a small amount of aluminum. It is also possible to perform using an additional cocatalyst.

When an olefinic polymer is prepared using the hybrid supported metallocene catalyst according to the present invention, an olefinic polymer having the broad molecular weight distribution and the BOCD structure wherein the SCB content at the low molecular weight side is low and the SCB content at the high molecular weight side is high can be prepared. Thus, the olefinic polymer has excellent physical properties as well as excellent workability.

For example, the olefinic polymer prepared by using the hybrid supported metallocene catalyst according to the present invention may have high weight average molecular weight of about 300,000 or more, or about 350,000 or more.

Furthermore, the hybrid supported metallocene catalyst according to the present invention has excellent activity, and the olefinic polymer prepared by using the hybrid supported metallocene catalyst according to the present invention shows, for example, a broad molecular weight distribution (PDI) of about 3.0 to about 8.0, preferably about 4.0 to about 8.0 and more preferably 5.0 to about 8.0, thereby providing excellent workability.

Hereinafter, the present invention will be specifically explained by way of the following examples. However, the examples of the present invention may be modified in various ways, and should not be construed as limiting the scope of the present invention.

EXAMPLES

Preparation Examples of the First Metallocene Compound

Preparation Example 1

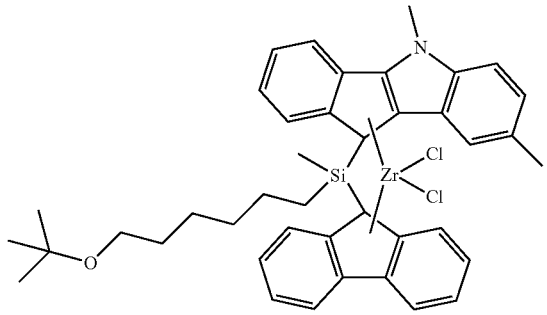

1-1 Preparation of Ligand Compound

Fluorene (2 g) was dissolved in MTBE (5 mL) and hexane (100 mL), and 2.5 M n-BuLi hexane solution (5.5 mL) was added dropwise in a dry ice/acetone bath and stirred overnight at room temperature. (6-(tert-butoxy)hexyl)dichloro(methyl)silane (3.6 g) was dissolved in hexane (50 mL), and fluorene-Li slurry was transferred under a dry ice/acetone bath for 30 minutes and stirred overnight at room temperature. At the same time, 5,8-dimethyl-5,10-dihydroindeno[1,2-b]indole (12 mmol, 2.8 g) was also dissolved in THF (60 mL), and 2.5M n-BuLi hexane solution (5.5 mL) was added dropwise in a dry ice/acetone bath and stirred overnight at room temperature.

The reaction solution of fluorene and (6-(tert-butoxy)hexyl)dichloro(methyl)silane was subjected to NMR sampling to confirm the completion of reaction. Thereafter, the 5,8-dimethyl-5,10-dihydroindeno[1,2-b]indole-Li solution was transferred under a dry ice/acetone bath and stirred overnight at room temperature. After reaction, the reaction mixture was extracted with ether/water and the remaining moisture in the organic layer was removed with MgSO$_4$ to give the ligand compound (Mw 597.90, 12 mmol). It was confirmed by 1H-NMR that two isomers were produced.

$^1$H NMR (500 MHz, d6-benzene): −0.30~−0.18 (3H, d), 0.40 (2H, m), 0.65~1.45 (8H, m), 1.12 (9H, d), 2.36~2.40 (3H, d), 3.17 (2H, m), 3.41~3.43 (3H, d), 4.17~4.21 (1H, d), 4.34~4.38 (1H, d), 6.90~7.80 (15H, m)

1-2 Preparation of Metallocene Compound

The ligand compound synthesized in 1-1 above (7.2 g, 12 mmol) was dissolved in diethylether (50 mL), and 2.5 M n-BuLi hexane solution (11.5 mL) was added dropwise in a dry ice/acetone bath and stirred overnight at room temperature. The mixture was dried under vacuum to give sticky oil having a brown color. This oil was dissolved in toluene to give a slurry. ZrCl$_4$(THF)$_2$ was prepared, and toluene (50 mL) was added thereto to prepare a slurry. The toluene slurry of ZrCl$_4$(THF)$_2$ (50 mL) was transferred in a dry ice/acetone bath. As the mixture was stirred overnight at room temperature, the color was changed to violet. The reaction solution was filtered to remove LiCl. The filtrate was dried under vacuum to remove toluene, hexane was added thereto, and the mixture was sonicated for 1 hour. The slurry was filtered to give the metallocene compound (6 g, Mw 758.02, 7.92 mmol, Yield 66 mol %) having a dark violet color as a filtered solid. Two isomers were observed through 1H-NMR.

$^1$H NMR (500 MHz, CDCl$_3$): 1.19 (9H, d), 1.71 (3H, d), 1.50~1.70 (4H, m), 1.79 (2H, m), 1.98~2.19 (4H, m), 2.58 (3H, s), 3.38 (2H, m), 3.91 (3H, d), 6.66~7.88 (15H, m)

Preparation Example 2

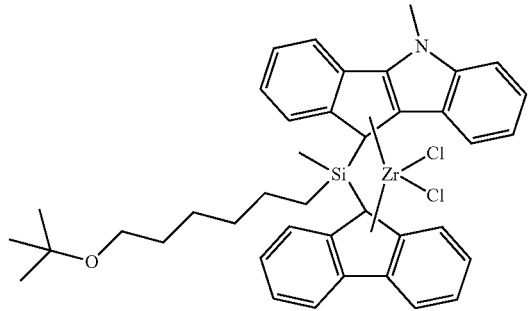

2-1 Preparation of Ligand Compound

To a 250 mL flask was introduced 5-methyl-5,10-dihydroindeno[1,2-b]indole (2.63 g, 12 mmol), which was then dissolved in THF (50 mL). Then, 2.5 M n-BuLi hexane solution (6 mL) was added dropwise in a dry ice/acetone bath and stirred overnight at room temperature. In another 250 mL flask, (6-(tert-butoxy)hexyl)dichloro(methyl)silane (1.62 g, 6 mmol) was prepared by dissolving it in hexane (100 mL), which was then slowly added dropwise to a lithiated solution of 5-methyl-5,10-dihydroindeno[1,2-b]indole under a dry ice/acetone bath and stirred overnight at room temperature. After reaction, the mixture was extracted with ether/water. The organic layer was treated with MgSO$_4$ to remove the remaining moisture and then dried under vacuum to give the ligand compound (3.82 g, 6 mmol) which was confirmed by 1H-NMR.

$^1$H NMR (500 MHz, CDCl3): −0.33 (3H, m), 0.86~1.53 (10H, m), 1.16 (9H, d), 3.18 (2H, m), 4.07 (3H, d), 4.12 (3H, d), 4.17 (1H, d), 4.25 (1H, d), 6.95~7.92 (16H, m)

2-2 Preparation of Metallocene Compound

The ligand compound synthesized in 2-1 above (3.82 g, 6 mmol) was dissolved in 18 toluene (100 mL) and MTBE (5 mL), and then 2.5 M n-BuLi hexane solution (5.6 mL, 14 mmol) was added dropwise in a dry ice/acetone bath and stirred overnight at room temperature. In another flask, ZrCl$_4$(THF)$_2$ (2.26 g, 6 mmol) was prepared as a slurry by adding toluene (100 mL). ZrCl$_4$(THF)$_2$ as a toluene slurry was transferred to the litiated ligand in a dry ice/acetone 4 bath. The mixture was stirred overnight at room temperature, and the color was changed to violet. The reaction solution was filtered to remove LiCl. The filtrate thus obtained was dried under vacuum, hexane was added thereto, and the mixture was sonicated. The slurry was filtered to give the metallocene compound (3.40 g, Yield 71.1 mole %) having a dark violet color as a filtered solid.

$^1$H NMR (500 MHz, CDCl3): 1.74 (3H, d), 0.85~2.33 (10H, m), 1.29 (9H, d), 3.87 (3H, s), 3.92 (3H, s), 3.36 (2H, m), 6.48~8.10 (16H, m)

Preparation Examples of the Second Metallocene Compound

Preparation Example 3 t-Butyl-O—(CH$_2$)$_6$—Cl was prepared using 6-chlorohexanol according to the method described in Tetrahedron Lett. 2951 (1988), and then reacted with NaCp to obtain t-Butyl-O—(CH$_2$)$_6$—C$_5$H$_5$ (Yield 60%, b.p. 80° C./0.1 mmHg).

Also, t-Butyl-O—(CH$_2$)$_6$—C$_5$H$_5$ was dissolved in THF at −78° C., n-BuLi was slowly added thereto, and the mixture was warmed up to room temperature and then reacted for 8 hours. Again at a temperature of −78° C., thus prepared lithium salt solution was slowly added to a suspension solution of ZrCl$_4$(THF)$_2$ (1.70 g, 4.50 mmol)/THF (30 ml) and the mixture was further reacted at room temperature for 6 hours.

All volatile substances were dried under vacuum and hexane solvent was added to the resulting oily liquid substance, which was then filtered. The filtrate was dried under vacuum, and hexane was added to induce a precipitate at a low temperature (−20° C.). The resulting precipitate was filtered at a low temperature to give [tBu-O—(CH$_2$)$_6$—C$_5$H$_4$]$_2$ZrCl$_2$ compound (Yield 92%) as a white solid.

$^1$H NMR (300 MHz, CDCl$_3$): 6.28 (t, J=2.6 Hz, 2H), 6.19 (t, J=2.6 Hz, 2H), 3.31 (t, 6.6 Hz, 2H), 2.62 (t, J=8 Hz), 1.7-1.3 (m, 8H), 1.17 (s, 9H).

$^{13}$C NMR (CDCl$_3$): 135.09, 116.66, 112.28, 72.42, 61.52, 30.66, 30.61, 30.14, 29.18, 27.58, 26.00.

Preparation Example 4

Preparation of (tBu-O—(CH$_2$)$_6$)(CH$_3$)Si(C$_5$(CH$_3$)$_4$)(tBu-N)TiCl$_2$

After Mg(s) (50 g) was introduced to a 10 L reactor at room temperature, and THF (300 mL) was added thereto. After I$_2$ (about 0.5 g) was added, the reactor was maintained at a temperature of 50° C. When the temperature of the reactor was stabilized, 6-t-butoxyhexyl chloride (250 g) was added to the reactor at a rate of 5 mL/min using a feeding pump. As 6-t-butoxyhexyl chloride was added, it was observed that the temperature of the reactor was elevated to about 4 to 5° C. The mixture was stirred for 12 hours while continuously adding 6-t-butoxyhexyl chloride. After the reaction for 12 hours, the black reaction solution was produced. 2 mL of this black solution was taken to which water was added to obtain an organic layer. The organic layer was confirmed to be 6-t-butoxyhexane through 1H-NMR. It could be seen from the above 6-t-butoxyhexane that Grignard reaction was well performed. Consequently, 6-t-butoxyhexyl magnesium chloride was synthesized.

MeSiCl$_3$ (500 g) and THF (1 L) were introduced to a reactor, and the temperature of the reactor was then cooled down to −20° C. The above synthesized 6-t-butoxyhexyl magnesium chloride (560 g) was added to the reactor at a rate of 5 mL/min using a feeding pump. After completion of the feeding of Grignard reagent, the mixture was stirred for 12 hours while slowly raising the temperature of the reactor up to room temperature. After the reaction for 12 hours, it was confirmed that white MgCl$_2$ salt was produced. Hexane (4 L) was added thereto and the salt was removed through a labdori to give a filtered solution. This filtered solution was added to the reactor, and hexane was then removed at 70° C. to give a liquid having a light yellow color. This liquid was confirmed to be the desired compound methyl(6-t-butoxyhexyl)dichlorosilane through 1H-NMR.

1H-NMR (CDCl3): 3.3 (t, 2H), 1.5 (m, 3H), 1.3 (m, 5H), 1.2 (s, 9H), 1.1 (m, 2H), 0.7 (s, 3H)

Tetramethylcyclopentadiene (1.2 mol, 150 g) and THF (2.4 L) were added to the reactor 14 and the temperature of the reactor was then cooled down to −20° C. n-BuLi (480 mL) was added to the reactor at a rate of 5 ml/min using a feeding pump. After adding n-BuLi, the mixture was stirred for 12 hours while slowly raising the temperature of the reactor up to room temperature. After the reaction for 12 hours, an equivalent of methyl(6-t-butoxyhexyl)dichlorosilane (326 g, 350 mL) was rapidly added to the reactor. The mixture was stirred for 12 hours while slowly raising the temperature of the reactor up to room temperature. Then, the temperature of the reactor was cooled to 0° C. again, and two equivalents of t-BuNH$_2$ was added. The mixture was stirred for 12 hours while slowly raising the temperature of the reactor up to room temperature. After the reaction for 12 hours, THF was removed. Hexane (4 L) was added and the salt was removed through a labdori to give a filtered solution. This filtered solution was added to the reactor again, and hexane was removed at 70° C. to give a solution having a yellow color. This yellow solution was confirmed to be the compound methyl(6-t-butoxyhexyl)(tetramethylCpH)t-butylaminosilane through 1H-NMR.

TiCl$_3$(THF)$_3$ (10 mmol) was rapidly added to the dilithium salt of the ligand at −78° C., which was synthesized from n-BuLi and ligand dimethyl(tetramethylCpH)t-Butylaminosilane in THF solution. While slowly warming the reaction solution from −78° C. to room temperature, it was stirred for 12 hours. After stirring for 12 hours, an equivalent of PbCl$_2$ (10 mmol) was added to the reaction solution at room temperature, and then stirred for 12 hours. After stirring for 12 hours, the dark black solution having a blue color was obtained. THF was removed from the reaction solution thus obtained before hexane was added and the product was filtered. Hexane was removed from the filtered solution, and then it was confirmed through 1H-NMR to be the desired (tBu-O—(CH$_2$)$_6$)(CH$_3$)Si(C$_5$(CH$_3$)$_4$)(tBu-N)TiCl$_2$ which is ([methyl(6-t-butoxyhexyl)silyl(η5-tetramethylCp)(t-butylamido)]TiCl$_2$).

1H-NMR (CDCl$_3$): 3.3 (s, 4H), 2.2 (s, 6H), 2.1 (s, 6H), 1.8~0.8 (m), 1.4 (s, 9H), 1.2 (s, 9H), 0.7 (s, 3H)

Preparation of Hybrid Supported Catalyst

Example 1

1-1 Drying of Support

Silica (SYLOPOL 948 manufactured by Grace Davison Co.) was dehydrated at a temperature of 400° C. for 15 hours under vacuum.

1-2 Preparation of Supported Catalyst

The dried silica (10 g) was introduced to a glass reactor to which toluene (100 mL) was additionally added and stirred. 10 wt % methylaluminoxane (MAO)/toluene solution (50 mL) was added thereto, and slowly reacted while stirring at 40° C. Thereafter, the reaction solution was washed with a sufficient amount of toluene to remove an unreacted aluminum compound, and the remaining toluene was removed under reduced pressure. Toluene (100 mL) was added thereto again, to which the metallocene catalyst of Preparation Example 1 (0.25 mmol) dissolved in toluene was added together and reacted for 1 hour. After completion of the reaction, the metallocene catalyst of Preparation Example 3 (0.25 mmol) dissolved in toluene was added and further reacted for 1 hour. After completion of the reaction, the stirring was stopped and the toluene was removed by layer separation, to which anilinium borate (N,N-dimethylanilinium tetrakis(pentafluorophenyl)borate, AB) (1.0 mmol) was added and stirred for 1 hour. Toluene was then removed at 50° C. under reduced pressure to give the supported catalyst.

Example 2

The supported catalyst was prepared according to the same procedure as in Example 1, except that the metallocene catalyst of Preparation Example 2 (0.25 mmol) was used instead of the metallocene catalyst of Preparation Example 1 (0.25 mmol).

Example 3

The supported catalyst was prepared according to the same procedure as in Example 1, except that after completion of the reaction of the metallocene catalyst of Preparation Example 1 (0.25 mmol) for 1 hour, the metallocene catalyst of Preparation Example 4 (0.25 mmol) was additionally reacted for 1 hour, and then the metallocene catalyst of Preparation Example 3 (0.25 mmol) was reacted.

Example 4

The supported catalyst was prepared according to the same procedure as in Example 3, except that the metallocene catalyst of Preparation Example 2 (0.25 mmol) was reacted, instead of the metallocene catalyst of Preparation Example 1 (0.25 mmol) first reacted in Example 3.

Example 5

The supported catalyst was prepared according to the same procedure as in Example 3, except that, instead of the metallocene catalyst of Preparation Example 1 (0.25 mmol) first reacted in Example 3, the metallocene catalyst of Preparation Example 2 (0.25 mmol) was first reacted, the metallocene catalyst of Preparation Example 1 (0.25 mmol) was then used as the second catalyst, and finally the metallocene catalyst of Preparation Example 3 was used.

Comparative Example 1

The dried silica (10 g) was introduced to a glass reactor to which toluene (100 mL) was additionally added and stirred. 10 wt % methylaluminoxane (MAO)/toluene solution (50 mL) was added thereto, and slowly reacted while stirring at 40° C. Thereafter, the reaction solution was washed with a sufficient amount of toluene to remove an unreacted aluminum compound, and the remaining toluene was removed under reduced pressure. Toluene (100 mL) was added thereto again, to which the metallocene catalyst of Preparation Example 3 (0.25 mmol) dissolved in toluene was added together and reacted for 1 hour. After completion of the reaction, toluene was removed at 50° C. under reduced pressure to give the supported catalyst.

Comparative Example 2

The supported catalyst was prepared according to the same procedure as in Comparative Example 1, except that the metallocene catalyst of Preparation Example 4 (0.25 mmol) was used instead of the metallocene catalyst of Preparation Example 3 (0.25 mmol) first reacted in Comparative Example 1.

Comparative Example 3

The supported catalyst was prepared according to the same procedure as in Comparative Example 2, except that after the reaction of the metallocene catalyst of Preparation Example 4 (0.25 mmol) first reacted in Comparative Example 2, the metallocene catalyst of Preparation Example 3 (0.25 mmol) was additionally reacted.

Comparative Example 4

The supported catalyst was prepared according to the same procedure as in Comparative Example 3, except that anilinium borate (N,N-dimethylanilinium tetrakis(pentafluorophenyl)borate, AB) (1.0 mmol) was added at the final stage of Comparative Example 3.

Experimental Example

Copolymerization of Ethylene-1-hexene 50 mg of each supported catalyst prepared in Examples 1 to 5 and Comparative Examples 1 to 4 was weighed in a dry box and introduced to a 50 mL glass bottle. The bottle was sealed with a rubber diaphragm and taken out of the dry box to prepare a catalyst for injection. The polymerization was performed in a 2 L metal alloy reactor equipped with a mechanical stirrer and capable of controlling temperature and being used under high pressure.

1 L of hexane containing 1.0 mmol of triethylaluminum, and 1-hexene (5 mL) were introduced to the reactor, and then each of the prepared supported catalysts was introduced thereto without contact with air. Then, the polymerization was carried out for an hour at 80° C., while continuously providing a gaseous ethylene monomer under a pressure of 9 Kgf/cm$^2$. The polymerization was terminated by stopping the stirring and then exhausting the unreacted ethylene.

After most of the polymerization solvent thus obtained was filtered off, the resulting polymer was dried at 80° C. vacuum oven for 4 hours.

The polymerization conditions for the respective catalysts prepared above, the ethylene/1-hexene polymerization activity, the molecular weight and molecular weight distribution of the polymer obtained are shown in Table 1 below.

TABLE 1

| Section | Metallocene Catalyst (Preparation Example No.) | Use of Cocatalyst (Anilinium Borate) | Polymerization Activity (kg-PE/g-Cat.) | Molecular Weight (*10$^4$ g/mol) | Molecular Weight Distribution (MWD) |
|---|---|---|---|---|---|
| Example 1 | 1/3 | ○ | 10.2 | 32.0 | 6.3 |
| Example 2 | 2/3 | ○ | 9.2 | 36.0 | 6.8 |
| Example 3 | 1/4/3 | ○ | 8.9 | 40.2 | 5.4 |

TABLE 1-continued

| Section | Metallocene Catalyst (Preparation Example No.) | Use of Cocatalyst (Anilinium Borate) | Polymerization Activity (kg-PE/g-Cat.) | Molecular Weight (*10⁴ g/mol) | Molecular Weight Distribution (MWD) |
|---|---|---|---|---|---|
| Example 4 | 2/4/3 | ○ | 7.8 | 45.2 | 5.7 |
| Example 5 | 2/1/3 | ○ | 8.2 | 49.8 | 6.5 |
| Comparative Example 1 | 3 | X | 3.6 | 16.7 | 2.1 |
| Comparative Example 2 | 4 | X | 1.2 | 113.3 | 2.2 |
| Comparative Example 3 | 4/3 | X | 3.8 | 20.2 | 3.4 |
| Comparative Example 4 | 4/3 | ○ | 7.4 | 19.2 | 3.0 |

Referring to Table 1, it could be seen that Examples 1 to 5 relating to the hybrid supported catalysts of the present invention included two or more different types of metallocene compounds, but they could prepare the polymers showing much higher activity, higher molecular weight and broader molecular weight distribution than those of Comparative Examples which included only a single catalyst or a second metallocene compound.

What is claimed is:

1. A hybrid supported metallocene catalyst which comprises at least one first metallocene compound selected from the group consisting of

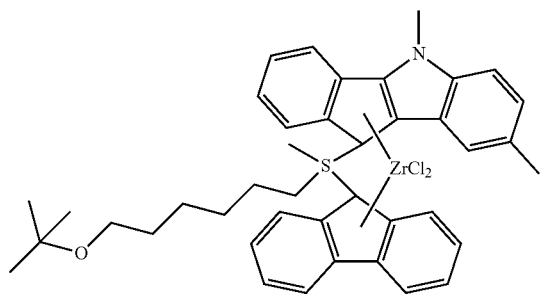

and

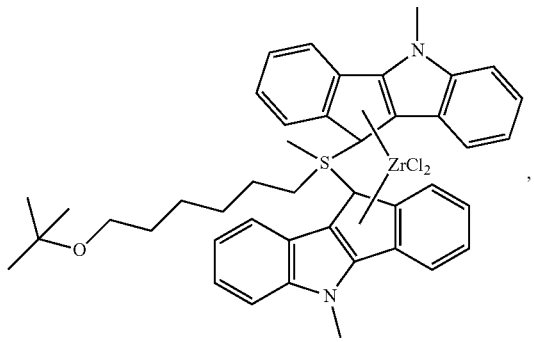

at least one second metallocene compound selected from the group consisting of [tBu-O—$(CH_2)_6$—$C_5H_4]_2ZrCl_2$ and [tBu-O—$(CH_2)_6(CH_3)Si(C_5(CH_3)_4](tBu-N)TiCl_2$, a cocatalyst compound and a support, wherein the cocatalyst comprises a first cocatalyst represented by the following Chemical Formula 6 and a second cocatalyst compound represented by the following Chemical Formula 7:

—[Al($R_{18}$)—O—]$_k$—      [Chemical Formula 6]

in Chemical Formula 6, $R_{18}$ is independently halogen, or unsubstituted or halogen-substituted hydrocarbyl group having 1 to 20 carbon atoms; and k is an integer of 2 or more, $T^+[BG_4]^-$      [Chemical Formula 7]

in Chemical Formula 7, $T^+$ is N,N-dimethylanilinium, B is boron in an oxidation state of +3, and G is pentafluorophenyl.

2. The hybrid supported metallocene catalyst according to claim 1 wherein the weight ratio of the transition metal in the first metallocene compound and the second metallocene compound to the support is 1:10 to 1:1.000.

3. The hybrid supported metallocene catalyst according to claim 1 wherein the weight ratio of the cocatalyst compound to the support is 1:1 to 1:100.

* * * * *